US00PP30702P3

(12) United States Plant Patent
Dyck

(10) Patent No.: US PP30,702 P3
(45) Date of Patent: Jul. 16, 2019

(54) SHRUB ROSE PLANT NAMED 'AAC576'

(50) Latin Name: *Rosa hybrida*
Varietal Denomination: AAC576

(71) Applicant: Her Majesty the Queen in Right of Canada (as represented by the Minister of Agriculture & Agri-Food), Lacombe (CA)

(72) Inventor: Larry Dyck, Morden (CA)

(73) Assignee: Her Majesty the Queen in Right of Canada (as represented by the Minister of Agriculture & Agri-food), Lacome, Alberta (CA)

( * ) Notice: Subject to any disclaimer, the term of this patent is extended or adjusted under 35 U.S.C. 154(b) by 0 days.

(21) Appl. No.: 15/731,750

(22) Filed: Jul. 28, 2017

(65) Prior Publication Data

US 2019/0037743 P1 Jan. 31, 2019

(30) Foreign Application Priority Data

Aug. 4, 2016 (CA) ..... PBR 16/8992

(51) Int. Cl.
*A01H 5/02* (2018.01)
*A01H 6/74* (2018.01)

(52) U.S. Cl.
USPC ..... Plt./108
CPC ..... *A01H 6/749* (2018.05)

(58) Field of Classification Search
USPC ..... Plt./101, 102, 108
See application file for complete search history.

(56) References Cited

U.S. PATENT DOCUMENTS

PP9,210 P 7/1995 Svejda
PP23,288 P2 1/2013 Richer

OTHER PUBLICATIONS

Retrieved from the Internet at http://www.houzz.com/discussions/4491805/canadian-shield-rose on Jun. 27, 2018 (3 pages).*

* cited by examiner

*Primary Examiner* — Susan McCormick Ewoldt
(74) *Attorney, Agent, or Firm* — Buchanan Ingersoll & Rooney PC

(57) ABSTRACT

A new and distinct variety of shrub rose plant herein referred to by its cultivar name, 'AAC576', is provided that abundantly forms attractive very full red blossoms. The plant exhibits an upright and bushy growth habit. The foliage is medium green with a glossy finish. The red blossom coloration contrasts nicely with the medium green foliage. The plant is well suited for providing attractive ornamentation in the landscape.

5 Drawing Sheets

BOTANICAL/COMMERCIAL CLASSIFICATION

Figure 1:
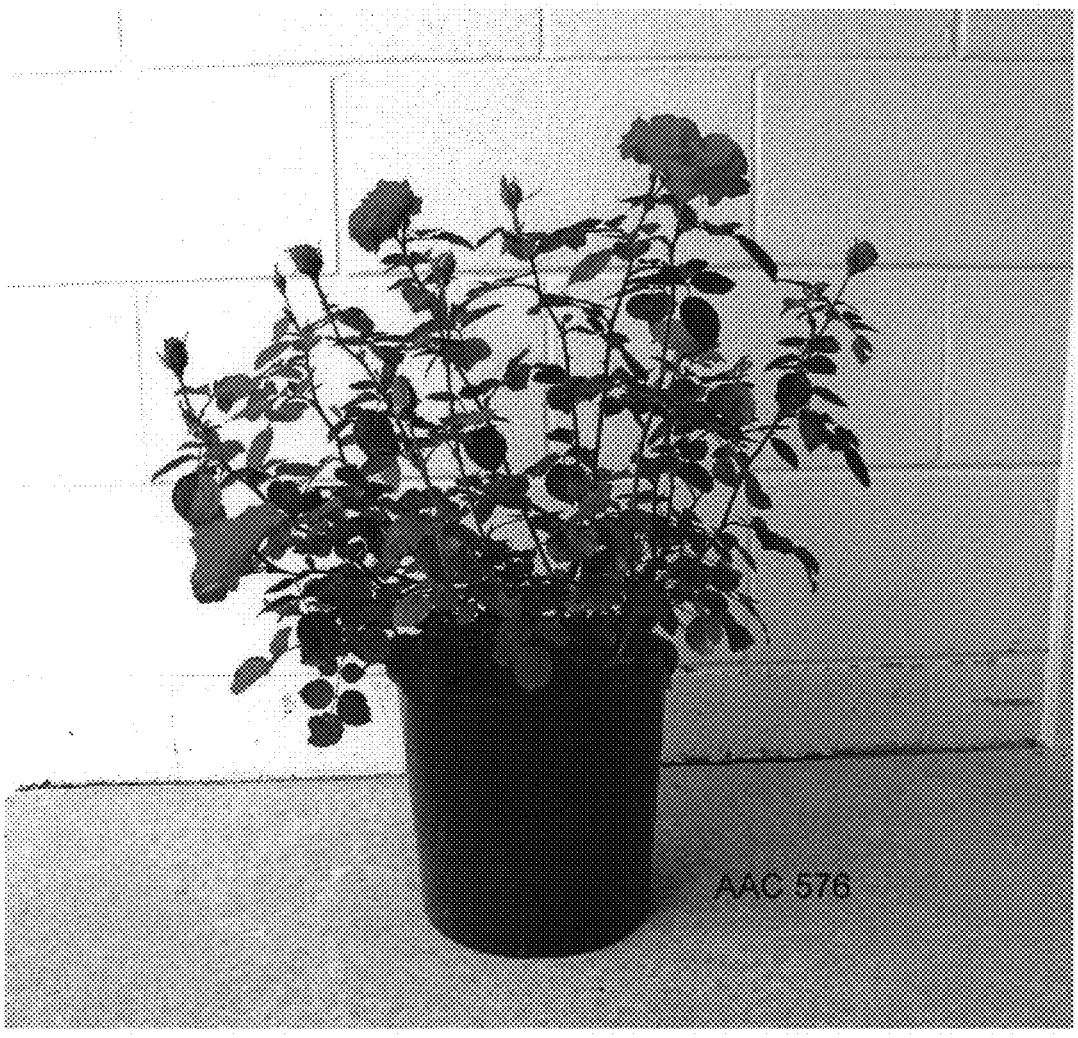

Latin name: *Rosa hybrida.*
Common name: Shrub Rose Plant.
Varietal denomination: 'AAC576'.

CROSS-REFERENCE TO RELATED APPLICATIONS

This application claims priority to Plant Breeders' Rights Application Number 16-8992, which was filed in Canada on Aug. 4, 2016, of which the content of is hereby expressly incorporated by reference in its entirety for all purposes.

SUMMARY OF THE INVENTION

The new and distinct variety of *Rosa hybrida* shrub rose plant was created by artificial pollination wherein two parents which previously had been studied were crossed in the hope that they would contribute the desired characteristics. The cross and selections were performed in Manitoba, Canada. The female parent (i.e., the seed parent) of the new variety was an unreleased and unpatented variety identified as 'Y8'. The male parent (i.e., the pollen parent) was the 'Frontenac' variety (U.S. Plant Pat. No. 9,210). The parentage of the new variety can be summarized as follows:

'Y8' x 'Frontenac'.

The initial cross was performed in 2001. The seeds resulting from the above pollination were sown and small plants were obtained which were physically and biologically different from one another. Seedlings from the cross were planted in an outdoor field in the Spring of 2002. In 2003, seedlings were evaluated and a single seedling possessing desired characteristics was identified. Initial cuttings of the selected seedling were taken in 2004 and maintained in a greenhouse until 2006, when three plants were planted in an outdoor test bed at Morden, Manitoba, Canada. In 2010 and 2011, all of the selected material was moved to Portage La Prairie, Manitoba, Canada. In April 2011 the new variety was moved to Vineland, Ontario along with other germ plasm for additional evaluation.

Had the new variety not been discovered and preserved it would have been lost to mankind. The new variety well meets the needs of the horticulture industry and is particularly well suited for growing in the landscape.

It was found that the new shrub rose plant of the present invention possesses the following combination of characteristics:

(a) abundantly and substantially continuously forms attractive very full red blossoms,
(b) exhibits an upright and bushy growth habit,
(c) forms attractive medium green foliage with a glossy finish that contrasts well with the red blossom coloration, and
(d) is well suited for growing as attractive ornamentation in the landscape.

The new variety well meets the needs of the horticultural industry and can be grown to advantage in the landscape, including parks, gardens, public areas, and residential landscapes, where attractive ornamentation is to be provided.

The new variety can be readily distinguished from its ancestors. More specifically, while the new variety displays red colored flowers, the 'Frontenac' variety (i.e., the pollen parent) displays dissimilar flowers which are commonly approaching Red-Purple Group 68B on the upper surface when blooming and commonly approaching Read-Purple Group 70D on the under surface when blooming and the 'Y8' variety (i.e., the seed parent) has a cupped bloom form while the new variety has a rosette form. Additionally, the new variety can be readily distinguished from other shrub rose plants such as the 'Navy Lady' variety (U.S. Plant Pat. No. 23,288). For instance, the 'Navy Lady' variety forms blossoms that are full double in configuration and dark red in coloration, while the new variety's blossoms are lighter red in coloration and very full in configuration when compared to 'Navy Lady'. Additionally, the 'Navy Lady' variety typically grows to approximately 2-3 feet in height, on average, while the new variety typically grows to approximately 4-5 feet in height, on average in 5 year old unpruned plants.

The characteristics of the new variety have been found at Manitoba, Canada, to be homogeneous and stable and to be strictly transmissible from one generation to another by asexual propagation through the rooting of cuttings. Accordingly, the new variety reproduces in a true-to-type manner by such asexual propagation.

The new variety has been named 'AAC576', and is being marketed under the CANADIAN SHIELD Trademark.

BRIEF DESCRIPTION OF THE PHOTOGRAPH

The accompanying photographs show as nearly true as it is reasonably possible to make the same, in a color illustration of this character, typical specimens of the plant parts of the new variety. The illustrated rose plants of the new variety were approximately 1.5 years of age and were observed during July 2017 while growing outdoors in 3 gallon containers on their own roots since April, 2016 at Vineland Research and Innovations Centre Inc., located at Vineland Station, Ontario Canada.

FIG. 1—illustrates an abundantly flowering rose plant together with nicely contrasting medium green foliage in a potted container located in a plant nursery setting.

Figure 2:
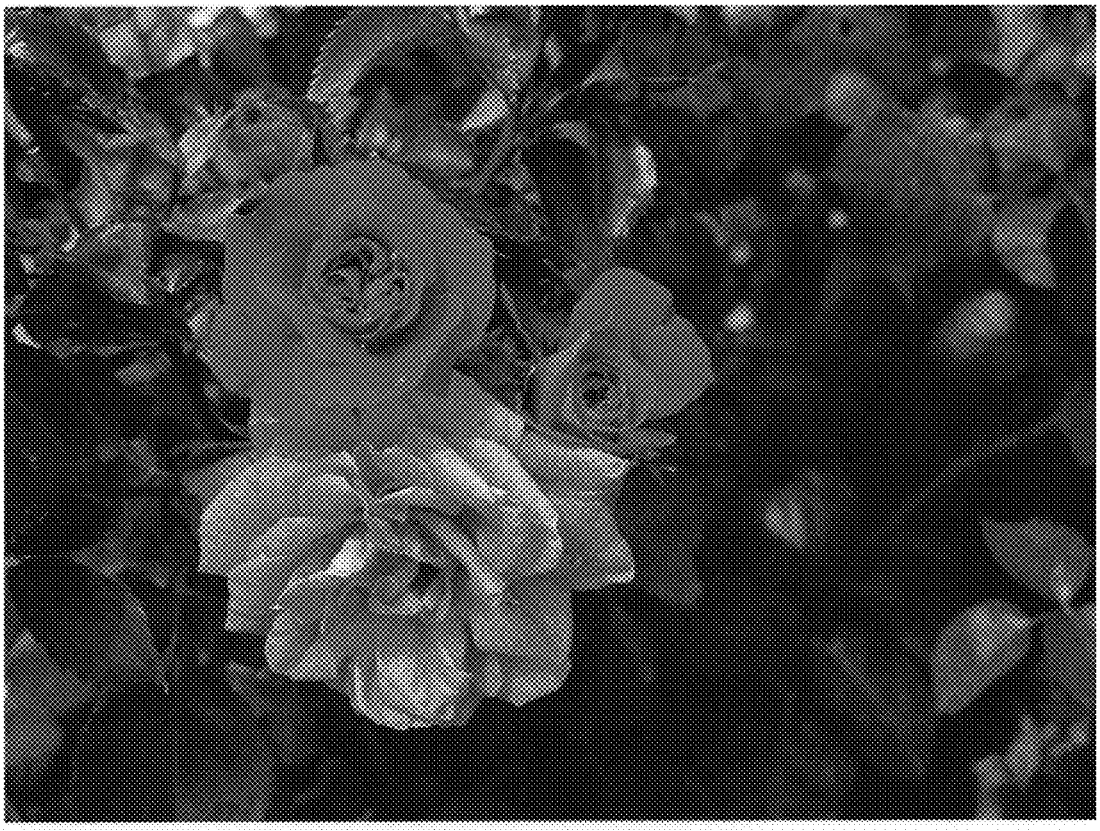

FIG. 2—illustrates a close enlarged view of the attractive very full configured red blossoms with a newly-opened blossom being shown at the top and a mature fully-opened blossom at the bottom on a plant growing in a nursery setting.

Figure 3:
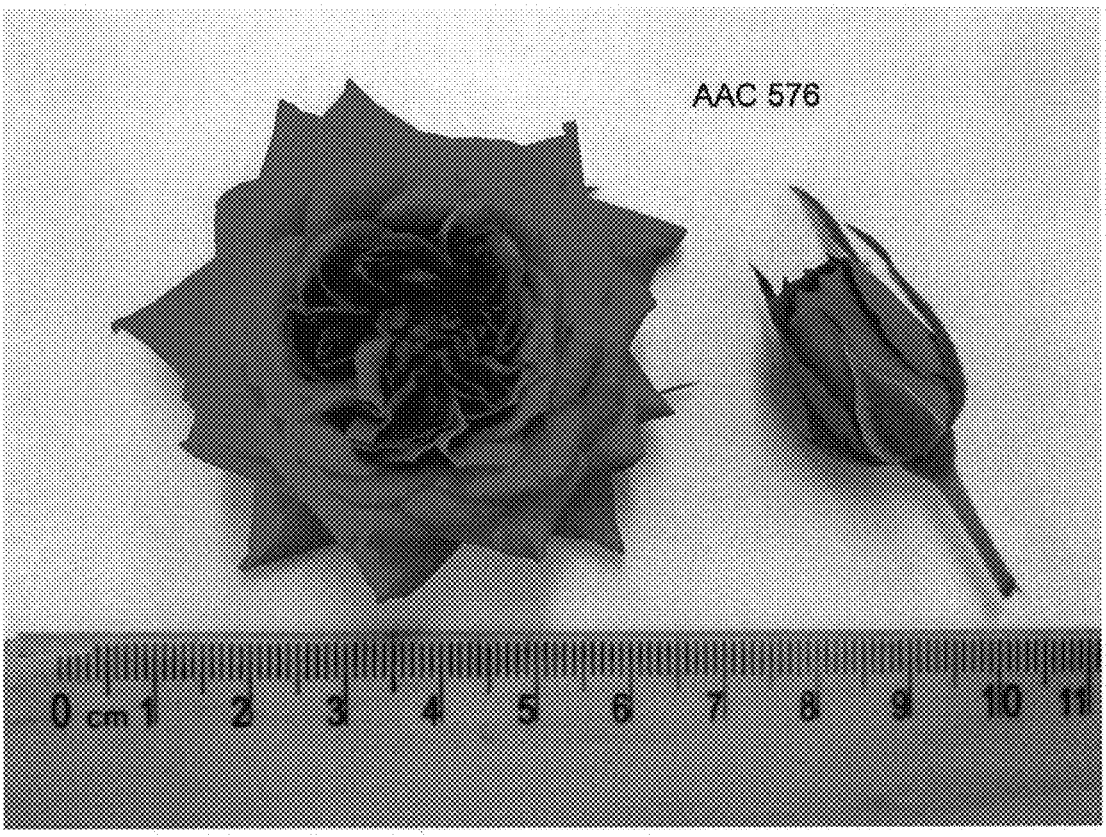

FIG. 3—illustrates a specimen of an open flower and a specimen of a bud; dimensions in centimeters are indicated at the bottom of the photograph.

Figure 4:
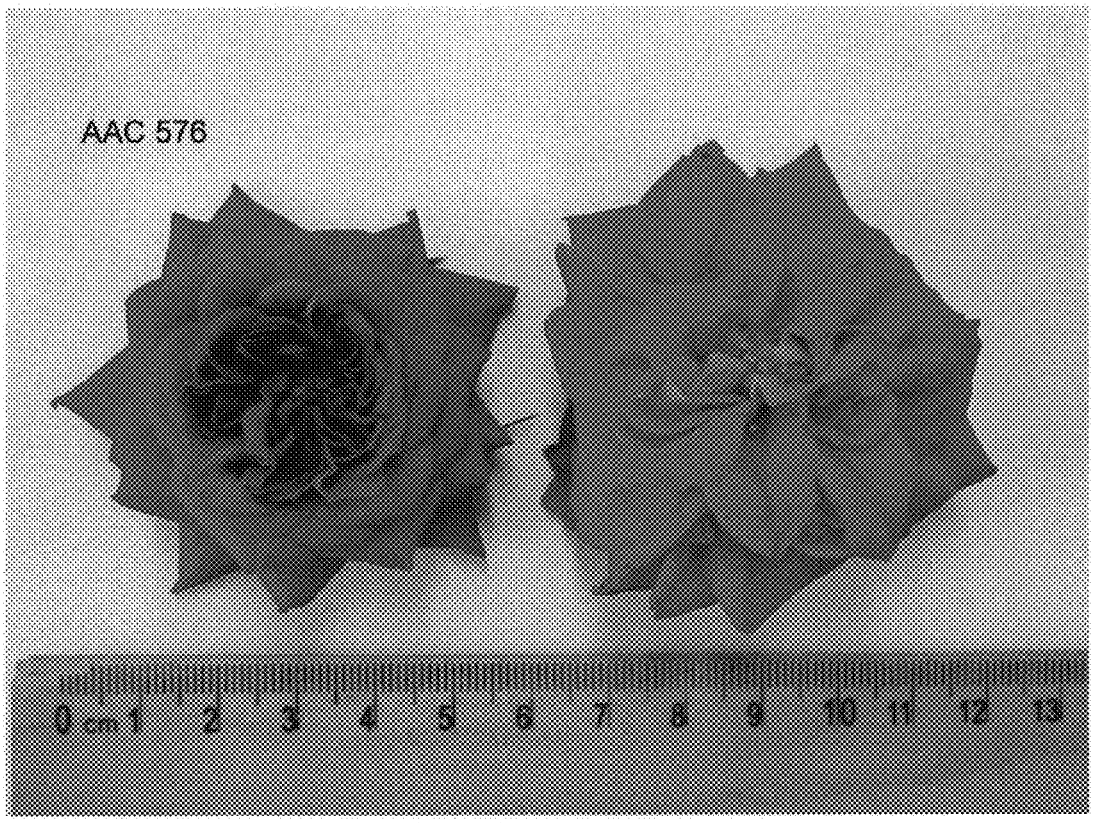

FIG. 4—illustrates two specimens of open flowers—top view; dimensions in centimeters are indicated at the bottom of the photograph.

Figure 5:
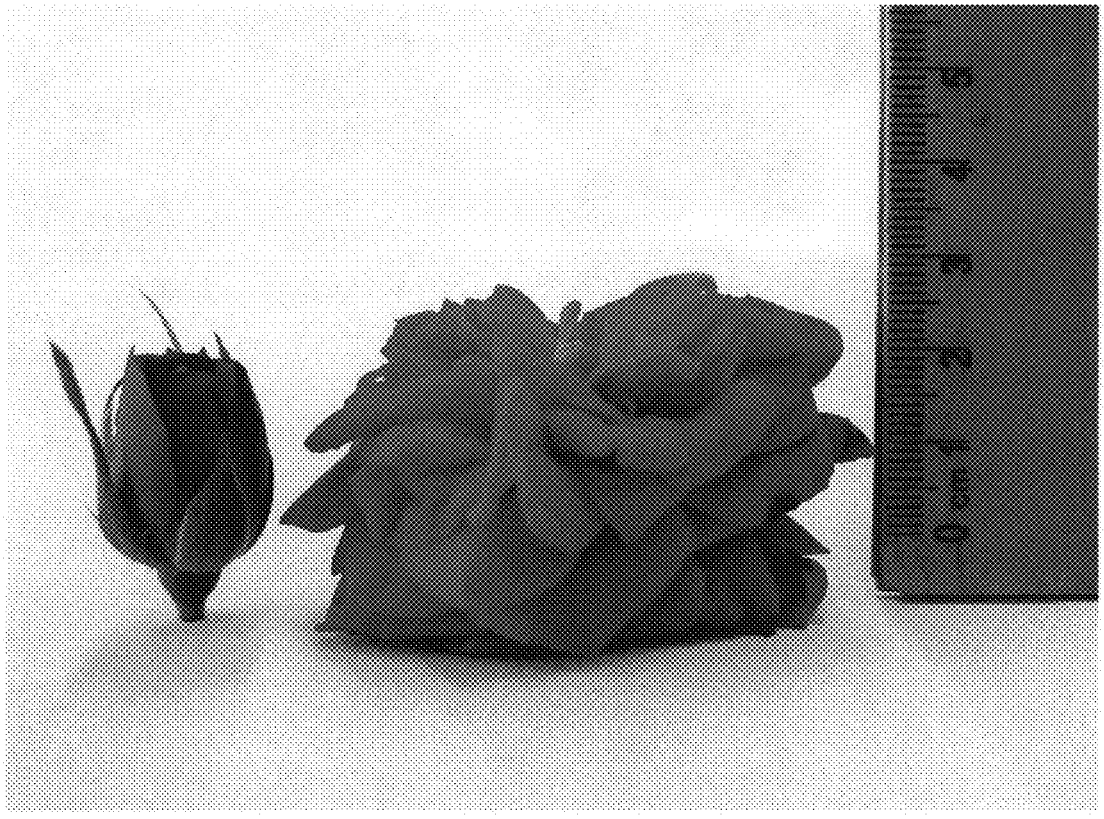

FIG. 5—illustrates a specimen of a bud and a specimen of an open flower—side view; dimensions in centimeters are indicated at the right of the photograph.

DETAILED BOTANICAL DESCRIPTION

The chart used in the identification of the colors is that of The Royal Horticultural Society ("R.H.S.") (R.H.S. Colour Chart, 2007 Edition). The description is based on the observation of plants 1.5 years of age during July of 2017 while growing outdoors on their own roots at Vineland Research and Innovations Centre Inc., located at Vineland Station, Ontario Canada.

Class: Shrub Rose. Variety 'AAC576'.

Plant:
- *Growth habit.*—Upright and bushy.
- *Height.*—Approximately 46 cm on average.
- *Width.*—Approximately 42 cm on average.

Branches:
- *Color.*—Commonly near Yellow-Green Group 146B on young stems and commonly near Yellow-Green Group 144A on mature stems/old wood.
- *Thorns.*—Young thorn: length is approximately 3 mm on average and color is commonly near Red-Purple Group 59A. Mature thorn: length is approximately 4-8 mm on average and color is commonly near Red-Purple Group 59A.

Foliage:
- *General appearance.*—Medium green with a glossy finish.
- *Number of leaflets.*—Commonly 5-7.
- *Terminal leaflet size.*—Approximately 3.7 cm on average in length and approximately 3.2 cm on average in width.
- *Lower leaflet size.*—Approximately 2.7 cm on average in length and approximately 1.5 cm on average in width.
- *Overall leaf size.*—Approximately 10.8 cm on average in length and approximately 6.9 cm on average in width.

Leaflets:
- *Shape.*—Ovate.
- *Margin type.*—Serrate.
- *Texture.*—Smooth.
- *Color.*—Young leaflet: upper surface is commonly near Greyed-Brown Group N199C and under surface is commonly Greyed-Red Group 178A. Mature leaflet: upper surface is commonly near Green Group N137C and under surface is commonly near Yellow-Green Group 147B.
- *Vein.*—Pattern: pinnate, cross-venulate. Color commonly near Yellow-Green Group 144A.
- *Stipules.*—Size: length is approximately 18 mm on average and diameter is approximately 12 mm on average. Color: commonly near Green Group 137B. Margin: spiny. Texture: smooth.

Inflorescence:
- *Number of blossoms per cluster.*—Commonly 2-6 on average.
- *Typical number of blossoms per plant.*—Commonly 8-10 on average.
- *Bloom season.*—Commonly June to October.

*Peduncle*.—Color: commonly near Yellow-Green Group 144A. Size: length is approximately 2.6 cm on average and width is approximately 2.5 mm on average.

*Sepal*.—Size: length is approximately 2.6 cm on average and width is approximately 8 mm on average. Color: upper surface is commonly near Yellow-Green Group 146B may have anthocyanin near Greyed-Purple Group 1878; under surface is commonly near Green Group 138B. Number: commonly 5. Margin type: weak to medium extensions.

*Bud*.—Shape: deltoid. Size: length is approximately 2.85 cm on average and diameter is approximately 1.45 cm on average.

*Flower*.—Form: very full. Petal number: approximately 29 on average. Petal size: approximately 2.9 cm on average in length and approximately 2.6 cm on average in width. Petal shape: generally round with an obcordate apex and a round base. Petal margin: type: entire. Petal drop: drop clean. Size: approximately 6.2 cm on average in diameter and approximately 2.8 cm on average in depth. Color: when opening: outermost petal upper surface is commonly near Red Group 53C and outermost petal lower surface is commonly near Red Group 45B. Color when fully open: upper surface is commonly near Red Group 45B and white at base attachment point; and lower surface is commonly near Red Group 53C. Fragrance: weak. Stamen number: approximately 50 on average. Anther: approximately 2.6 mm on average in length, sagittate in shape, and color is commonly near Greyed-Orange Group N167D. Filament: approximately 4 mm on average in length and commonly near Yellow Group 11A in color. Pistil number: approximately 68 on average. Stigma: length commonly varies from 2 mm to 7 mm, shape is discoid, and color is commonly near Yellow Group 10B. Style: length is approximately 3.5 mm on average and color is commonly pale yellow to pale pink.

*Receptacle*.—Shape: globular Size: length is approximately 5.2 mm on average and width is approximately 7.9 mm on average. Color: commonly near Yellow-Green Group 144A with weak anthocyanin.

*Hips/seed*.—Occasionally present.

Development:

*Vegetation*.—Vigorous.

*Blooming*.—Repeat blooming; abundant and substantially continuous.

*Resistance to diseases*.—Very tolerant to powdery mildew *Sphaerotheca pannosa*, downy mildew *Peronospora sparsa*, rust *Phragmidium* spp., *Cercosprora rosicola*, and black spot *Diplocarpon rosae* as a potted plant under normal growing conditions.

The new 'AAC576' variety has not been observed under all possible environmental conditions to date. Accordingly, it is possible that the phenotypic expression may vary somewhat with changes in light intensity and duration, cultural practices, and other environmental conditions.

I claim:

1. A new and distinct shrub rose plant characterized by the following combination of characteristics:

(a) abundantly and substantially continuously forms attractive very full red blossoms, (b) exhibits an upright and bushy growth habit, (c) forms attractive medium green foliage with a glossy finish that contrasts well with the red blossom coloration, and (d) is well suited for growing as attractive ornamentation in the landscape;

substantially as herein shown and described.

* * * * *